US008158066B2

(12) United States Patent
Yang

(10) Patent No.: US 8,158,066 B2
(45) Date of Patent: Apr. 17, 2012

(54) AROMA LAMP STRUCTURE

(76) Inventor: Chin-Sheng Yang, Tainan (TW)

( * ) Notice: Subject to any disclaimer, the term of this patent is extended or adjusted under 35 U.S.C. 154(b) by 208 days.

(21) Appl. No.: 12/762,375

(22) Filed: Apr. 19, 2010

(65) Prior Publication Data

US 2010/0272615 A1    Oct. 28, 2010

(30) Foreign Application Priority Data

Apr. 28, 2009   (TW) .............................. 98205693 U

(51) Int. Cl.
*A62B 7/08*      (2006.01)
*G09F 19/00*     (2006.01)
*A63H 23/08*     (2006.01)
(52) U.S. Cl. .......................... 422/124; 40/406; 446/267

(58) Field of Classification Search ................... 422/124; 40/406; 446/267
See application file for complete search history.

(56) References Cited

U.S. PATENT DOCUMENTS

| 7,905,426 B1 * | 3/2011 | Greiner ........................... 239/44 |
| 2006/0128258 A1 * | 6/2006 | Zebert et al. ................... 446/166 |

* cited by examiner

*Primary Examiner* — Kevin Joyner
(74) *Attorney, Agent, or Firm* — Leong C. Lei

(57) ABSTRACT

The aroma lamp contains a transparent, three-dimensional body member with a viscous fluid and a paddling element configured inside. The body member is placed on top of a base member, inside which an aroma producing element and light generating elements are provided. Additionally, a driving element spinning a fan element to disperse aroma and a magnet engaging the paddling element is also housed inside the base member. As such, the aroma lamp produces visually appealing effect by the light projected from the light generating element while disperses aroma by the fan element's air flow.

4 Claims, 3 Drawing Sheets

AROMA LAMP STRUCTURE

TECHNICAL FIELD OF THE INVENTION

The present invention generally relates to aroma lamps, and more particular to an aroma lamp using interacting magnetic elements to spin a fan to create appealing visual effect and to disperse aroma.

DESCRIPTION OF THE PRIOR ART

Table decorators such as photo frames are common in daily life. Usually they are in a visually appealing yet static design. On the other hand, there are so-called snow globes where a transparent sphere enclosing a miniaturized scene or landscape and water with particles or spangles in the globe. When the globe is shaken, the particles or spangles are churned up and then fall or flow in the water to create an interesting visual effect. Usually some lamp is also integrated so that the particles or spangles reflect the light from the lamp to create an even more appealing and glistening visual effect.

SUMMARY OF THE INVENTION

Therefore, a novel aroma lamp is provided herein. The aroma lamp contains a transparent, three-dimensional body member with a viscous fluid and a paddling element configured inside. The body member is placed on top of a base member, inside which an aroma producing element and light generating elements are provided. Additionally, a driving element spinning a fan element to disperse aroma and a magnet engaging the paddling element is also housed inside the base member. As such, the aroma lamp produces visually appealing effect by the light projected from the light generating element while disperses aroma by the fan element's air flow.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
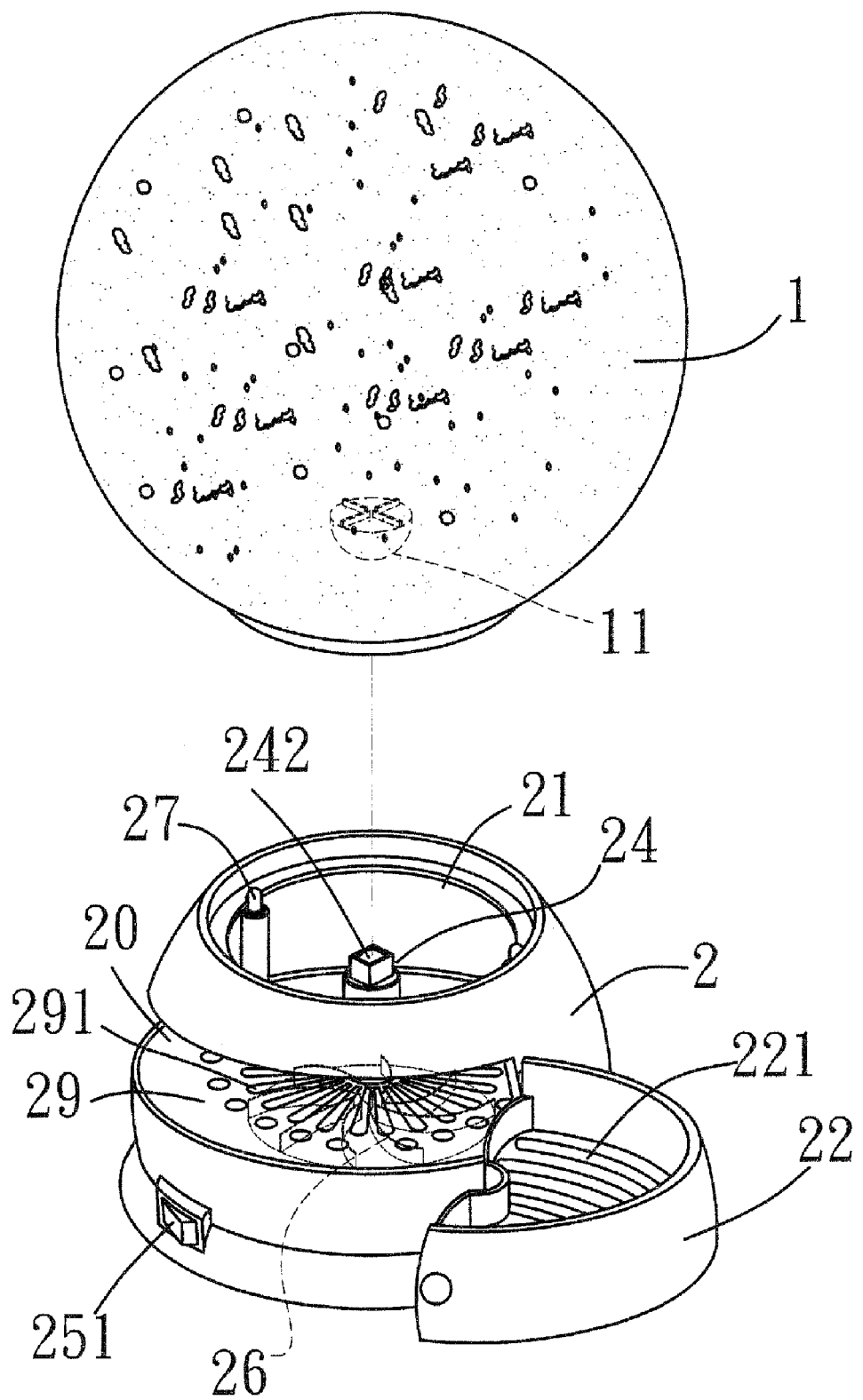
FIG. 1 is a perspective break-down diagram showing the various components of an aroma lamp according to an embodiment of the present invention.
Figure 2:
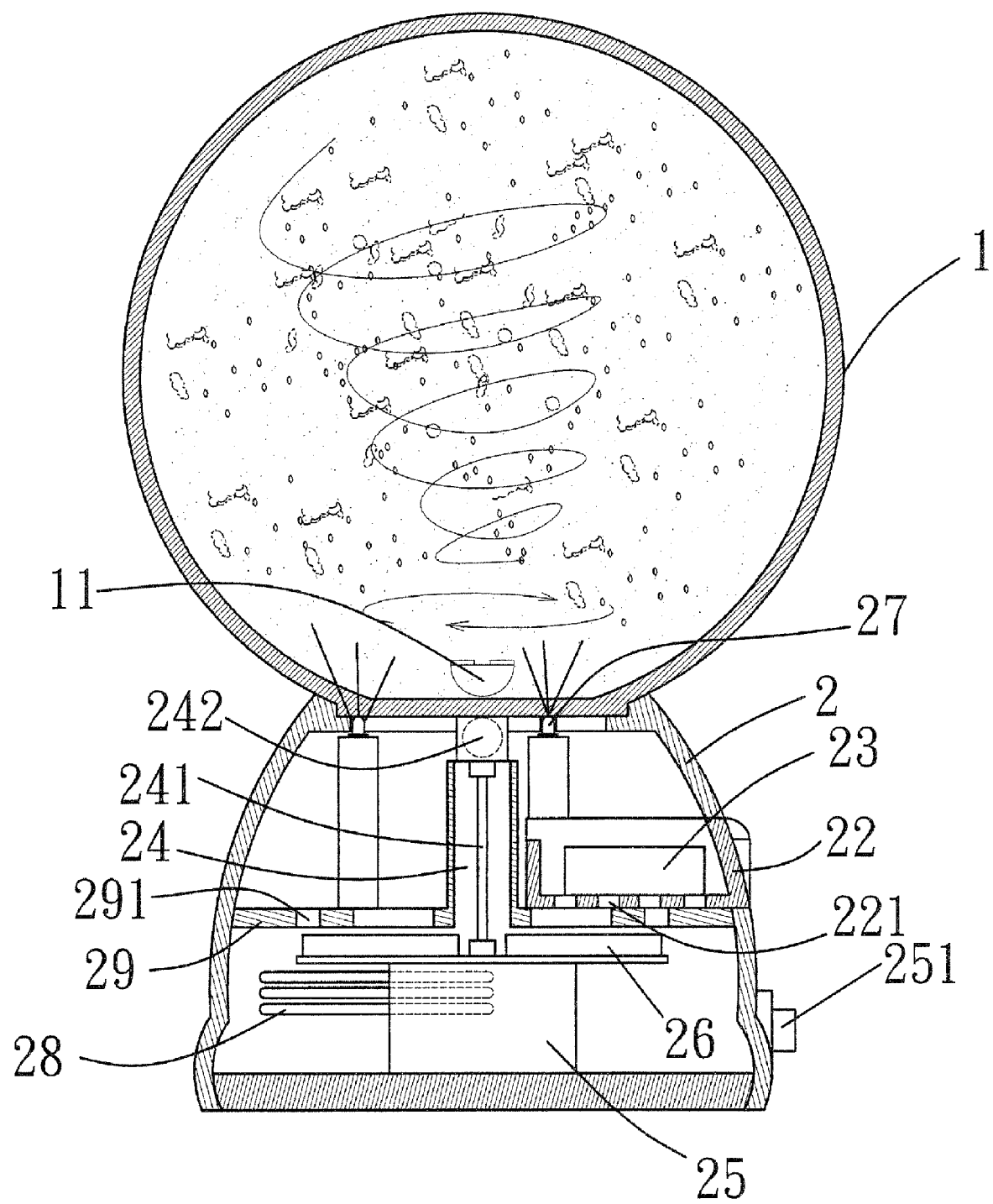
FIG. 2 is a sectional diagram showing the aroma lamp of FIG. 1.
Figure 3:
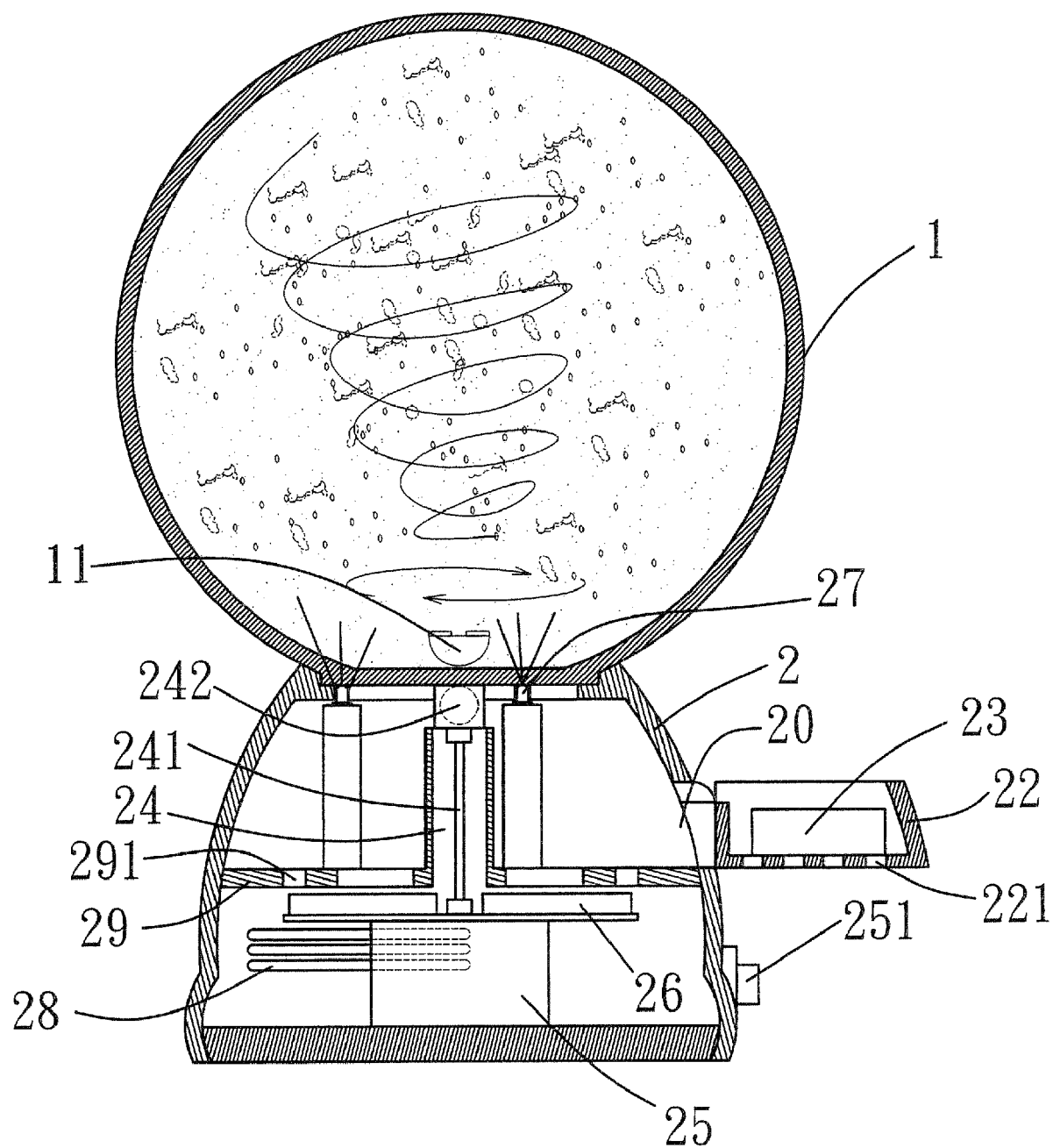
FIG. 3 is a sectional diagram showing the aroma lamp of FIG. 1 where a tray for holding aroma producing element is opened.

As shown in FIGS. 1 and 2, an aroma lamp according to an embodiment of the present invention contains a body member 1 and a base member 2.

The body member 1 is a transparent, three-dimensional, hollow shape and a viscous flowing fluid is sealed inside. A magnetically engaged paddling element 11 is also configured inside the body member 1.

The base member 2 has a top opening 21 to receive the body member 1. A tray 22 is housed in a lateral indentation 20 and hinged to the opening of the lateral indentation 20 of the base member 2. The tray 22 is to hold an aroma producing element 23 and there are a number of through holes 221 on a bottom surface of the tray 22 beneath the aroma producing element 23. Inside the base member 2, an axle element 24 magnetically engaging the paddling element 11 is housed. The axle element 24 is extended vertically from a fan element 26 and the two are together driven to spin by a driving element 25. The axle element 24 is right beneath the paddling element 11 and the fan element 26 is beneath the tray 22.

Light emitting diodes (LEDs) 27 are provided at the top opening 21 of the base member 2 so that light beams are projected into the body member 1. The driving element 5 is turned on and off by a switch 251 exposed outside the base member 2, and draws electricity from an internal battery or some external DC or AC power source. The power source is not the subject matter of the present invention and its detail is omitted here.

The tray 22 could be swung out of the lateral indentation 20 for the replacement of aroma producing element 23 and then swung back into the lateral indentation 20. When the driving element 25 is turned on by the switch 251, the driving element 25 causes the axle element 24 and the fan element 26 to spin. In the present embodiment, the axle element 24 contains an axle 241 with a magnet 242 on a top end. The fan element 26 blows air into the tray 22 through the through holes 221 so as to boost the aroma from the aroma producing element 23 to spread. Additionally, a partition plate 29 with through holes 291 is positioned between the tray 22 and the fan element 26. The LEDs 27 are raised from the partition plate 29 so that they are located at the top opening 21. When the body member 1 is placed on the base member 2 and received by the top opening 21, the paddling element 11 inside the body member 1 is positioned correspondingly with the magnet 242 of the axle element 24.

When the driving element 25 is turned on by the switch 251, the driving element 25 causes the axle element 24 (therefore, the magnet 242) and the fan element 26 to spin. As such, the paddling element 11, magnetically engaged by magnet 242, is spun as well, churning the fluid inside the body member 1. In the mean time, air is blown upward by the fan element 26 to flow through the through holes 291, 221 to carry the aroma from the aroma producing element 23 and to exchange outside air through a number of slots 28 configured on the lateral surface of the base member 2. When the driving element 25 is turned on, the LEDs 27 are turned on as well to illuminate the body member 1 for visually appealing effect.

The aroma lamp as described above has a number of advantages. Firstly, the aroma lamp according to the present invention, by configuring fan element and magnet on the driving element, stirs up the fluid inside the body member and disperses the aroma from the aroma producing element, thereby not only creating appealing visual effect but also improving air quality of the environment.

Secondly, the aroma lamp according to the present invention provides LEDs beneath the body member so that the illumination further enhances the aroma lamp's visual appealing effect.

Thirdly, the aroma lamp according to the present invention provides easy and convenient replacement of the aroma producing element. Therefore, a user could choose his/her preferred aroma at will.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An aroma lamp, comprising:
   a transparent body member of a three-dimensional shape having a viscous fluid and a paddling element sealed inside; and
   a base member having a top opening to receive said body member, a tray holding an aroma producing element hinged to a lateral section of said base member and capable of being exposed and restored, a driving element, a magnetic axle element engaging said paddling element driven by said driving element to spin, a fan element beneath said tray driven by said driving element to spin.

2. The aroma lamp according to claim 1, wherein said base member has a plurality of light emitting diodes positioned at said top opening beneath said body member; and the light from said light emitting diodes is projected into said body member.

3. The aroma lamp according to claim 1, wherein said magnetic axle element contains an axle and a magnet at a top end of said axle.

4. The aroma lamp according to claim 1, wherein a plurality of slots are configured on a lateral section of said base member for exchanging aromatic air dispersed by said fan element with outside environmental air.

* * * * *